US006692754B1

(12) United States Patent
Makimoto et al.

(10) Patent No.: US 6,692,754 B1
(45) Date of Patent: Feb. 17, 2004

(54) COSMETIC COMPOSITION

(75) Inventors: Yutaka Makimoto, Machida (JP);
Asako Kobayashi, Tsukuba (JP);
Toshihiro Sakakibara, Machida (JP);
Chiemi Takaboshi, Tsukuba (JP);
Ayako Kamimura, Tsukuba (JP);
Tomoya Takahashi, Tsukuba (JP);
Minako Tajima, Tsukuba (JP);
Yoichiro Takekoshi, Rye, NY (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/914,599

(22) PCT Filed: Mar. 1, 2000

(86) PCT No.: PCT/JP00/01203

§ 371 (c)(1),
(2), (4) Date: Aug. 30, 2001

(87) PCT Pub. No.: WO00/51561

PCT Pub. Date: Sep. 8, 2000

(30) Foreign Application Priority Data

Mar. 2, 1999 (JP) .............................................. 11-53767

(51) Int. Cl.[7] .......................... A61K 7/48; A61K 31/401
(52) U.S. Cl. ...................... 424/401; 514/423; 514/477
(58) Field of Search ................................ 514/477, 423; 424/401

(56) References Cited

U.S. PATENT DOCUMENTS

| 5,362,494 A | * | 11/1994 | Zysman et al. .............. 424/401 |
| 6,039,939 A | | 3/2000 | Ley et al. ................. 424/78.03 |

FOREIGN PATENT DOCUMENTS

| EP | 0346189 | * | 12/1989 |
| FR | 261971 | * | 9/1987 |
| GB | 2 151 924 | | 7/1995 |
| JP | 01-131107 | | 9/1988 |
| JP | 01211512 | * | 8/1989 |
| JP | 05 59075 | | 9/1993 |
| JP | 05 339140 | | 12/1993 |
| JP | 11 49628 | | 2/1994 |
| JP | 06 19960 | | 7/1994 |
| JP | 07 313179 | | 12/1995 |
| JP | 07322885 | | 12/1995 |
| JP | 09 087126 | | 3/1997 |
| JP | 09 255552 | | 9/1997 |

* cited by examiner

*Primary Examiner*—Charles L. Patterson, Jr.
(74) *Attorney, Agent, or Firm*—Fitzpatrick, Cella, Harper & Scinto

(57) ABSTRACT

The present invention relates to skin aging inhibitors and/or skin quality-improving agents comprising hydroxyproline, its N-acyl derivatives or salts thereof, and cosmetic compositions for inhibiting skin aging and/or improving skin quality comprising said skin aging inhibitors and/or skin quality-improving agents.

4 Claims, No Drawings

COSMETIC COMPOSITION

TECHNICAL FIELD

The present invention relates to skin aging inhibitors and/or skin quality-improving agents, and cosmetic compositions having the activities to inhibit the skin aging and to improve the skin quality containing said skin aging inhibitors and/or skin quality-improving agents.

BACKGROUND ART

Aging preventive materials have so far been broadly employed in cosmetics for the purpose of attaining beauty effect for preventing skin aging or deterioration of skin quality which causes skin troubles such as wrinkles, bags, dry skin, etc.

The aging preventive materials employed in cosmetics are broadly classified into peroxide lipid inhibitors and cell activators. Examples of the materials having the activity to inhibit peroxide lipid are α-hydroxy acids, vitamin A, β-carotene, vitamin $B_{12}$, vitamin E, pigments such as plarutin and platonin, scutellaria root, rutin, sesame extract, and tea extract, etc. On the other hand, examples of the cell activators are muminequis, glycolic acid, γ-amino acid, sialic acid, royal jerry, extract of Swertia japonica (Schult.) Makino, Japanese chirata, ginseng extract, etc.

It is known that the cell activators include materials which promote collagen synthesis and materials having the activity to improve skin quality.

Examples of the materials which promote collagen synthesis include various growth factors such as transforming growth factor β1, platelet-derived growth factor, basic fibroblast growth factor and insulin-like growth factor 1, etc. and silk protein, etc.

Examples of the materials having the activity to improve the skin quality include allantoin, aloe extract, ginseng extract, placenta extract, bovine blood freed of protein, fermentation metabolites, and so on.

There is a report that hydroxyproline derivatives are used as components of cosmetics to keep the skin elasticity by increasing the oxygen consumption of disrupted mouse liver. (JP, 1-131107, A) However, the report contains neither description of the relationship between the increase in oxygen consumption of disrupted mouse liver and the effect on the human skin nor data concerning the effectiveness of compounds as components of cosmetics. Accordingly, it is not possible to conclude from the report that the hydroxyproline derivatives are effective as components of cosmetics. There has been no report showing that hydroxyproline or its derivatives are effective as cosmetics.

For the purpose of enhancing moisture retention effect, there are reports on cosmetics comprising mucin (JP, 5-339140, A) or glycine betaine and pyrrolidonecarboxylic acid or its salt (JP, 9-87126, A) in combination with amino acids. In the reports, hydroxyproline is mentioned as an example of amino acids, but no data is given concerning the effect of cosmetics comprising hydroxyproline.

In this way, any function and effect of hydroxyproline and its N-acyl derivatives to skin in the cosmetic field is unknown.

It is not known that hydroxyproline and its N-acyl derivatives show an activity to promote the proliferation of epidermal cells and an activity to promote the collagen synthesis in fibroblast. Further, any cosmetics utilizing said activity has not been known yet.

In addition, any cosmetics made of hydroxyproline manufactured by using a microorganism have never been known so far.

DISCLOSURE OF THE INVENTION

An object of the present invention is to provide skin aging inhibitors and/or skin quality-improving agents having the activity to inhibit the skin aging and/or the activity to imporve the skin quality, such as epidermis proliferation promoters, fibroblast collagen-synthesis promoters, epidermis moisture retention function-improving agents, and to provide cosmetic compositions having the activity to inhibit the skin aging and/or the activity to improve the skin quality containing said skin aging inhibitors and/or skin quality-improving agents.

An object of the present invention is to provide a method of inhibiting skin aging and/or improving skin quality which comprises applying onto skin a skin aging inhibitor and/or skin quality-improving agent containing hydroxyproline, its N-acyl derivative or salts thereof as an effective ingredient.

Another object of the present invention is to provide a method of inhibiting skin aging and/or improving skin quality which comprises applying skin aging inhibiting cosmetic compositions and/or skin quality-improving cosmetic compositions containing hydroxyproline, its N-acyl derivative or salts thereof as an effective ingredient onto skin.

A further object of the present invention is to provide use of hydroxyproline, its N-acyl derivative or salts thereof for producing skin aging inhibitors and/or skin quality-improving agents.

An object of the present invention is to provide use of hydroxyproline, its N-acyl derivative or salts thereof for producing cosmetic compositions having the activity to inhibit skin aging and/or to improve skin quality.

Another object of the present invention is to provide use of hydroxyproline, its N-acyl derivative or salts thereof for inhititing skin aging and/or improving skin quality.

As the result of keen investigations for cosmetics with high safety having moisture keeping effect, skin aging-inhibiting activity and skin quality-improving activity, the present inventors have found that hydroxyproline or N-acyl derivatives thereof shows such the effect, and thus, the present invention has been completed.

Accordingly, the present invention relates to the following features (1)–(68).

(1) Skin aging inhibitors and/or skin quality-improving agents, comprising hydroxyproline, N-acylated hydroxyproline derivatives or salts thereof.

(2) The skin aging inhibitors and/or skin quality-improving agents according to (1), wherein the amount of said hydroxyproline or N-acylated hydroxyproline derivatives is 0.01 to 5 wt % based on the total weight.

(3) The skin aging inhibitors and/or skin quality-improving agents according to (1) or (2), wherein said N-acylated hydroxyproline derivatives are N-acetylated hydroxyproline derivatives or N-propionated hydroxyproline derivatives.

(4) The skin aging inhibitors and/or skin quality-improving agents according to any one of (1) to (3), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(5) The skin aging inhibitors and/or skin quality-improving agents according to any one of (1) to (4), wherein said hydroxyproline is produced by using a microorganism.

(6) The skin aging inhibitors and/or skin quality-improving agents according to (5), wherein proline 3-hydroxylase or proline 4-hydroxylase gene derived from a microorganism belonging to a genus selected from the group consisting of the generaAmycolatopsis, Dactylosporangium and Streptomyces is introduced into the microorganism.

(7) The skin aging inhibitors and/or skin quality-improving agents according to any one of (1) to (6), wherein said skin aging inhibitors and/or skin quality-improving agents are agents for promoting the proliferation of epidermal cells.

(8) The skin aging inhibitors and/or skin quality-improving agents according to any one of (1) to (6), wherein said skin aging inhibitors and/or skin quality-improving agents are agents for promoting the collagen synthesis of fibroblast.

(9) The skin aging inhibitors and/or skin quality-improving agents according to any one of (1) to (6), wherein said skin aging inhibitors and/or skin quality-improving agents are agents for improving the moisture retention function of epidermis.

(10) The skin aging inhibitors and/or skin quality-improving agents according to any one of (1) to (6), wherein said skin aging inhibitors and/or skin improving agents are agents for inhibiting and/or improving the wrinkle formation.

(11) The skin aging inhibitors and/or skin quality-improving agents according to any one of (1) to (10), wherein said skin is human skin.

(12) Cosmetic compositions for inhibiting skin aging and/or improving skin quality, comprising said skin aging inhibitors and/or skin quality-improving agents according to any one of (1) to (11).

(13) The cosmetic compositions according to (12), wherein said hydroxyproline, N-acylated hydroxyproline derivatives or salts thereof are N-acetylhydroxyproline or its salt.

(14) The cosmetic compositions according to (12) or (13), wherein the cosmetic compositions contain at least one ingredient selected from the group consisting of lecithin, lysolecithin and hyaluronic acid.

(15) A method of inhibiting skin aging and/or improving skin quality, which comprises applying skin aging inhibitors and/or skin quality-improving agents containing hydroxyproline, N-acylated hydroxyproline derivatives or salts thereof as an effective ingredient onto skin.

(16) The method of inhibiting skin aging and/or improving skin quality according to (15), wherein said skin aging inhibitors and/or skin quality-improving agents contain 0.01 to 5 wt % of hydroxyproline, N-acylated hydroxyproline derivatives or salts thereof based on the total weight.

(17) The method of inhibiting skin aging and/or improving skin quality according to (15) or (16), wherein said N-acylated hydroxyproline derivatives are N-acetylated hydroxyproline derivatives or N-propionated hydroxyproline derivatives.

(18) The method of inhibiting skin aging and/or improving skin quality according to any one of (15) to (17), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(19) The method of inhibiting skin aging and/or improving skin quality according to any one of (15) to (18), wherein said hydroxyproline is produced by using a microorganism.

(20) The method of inhibiting skin aging and/or improving skin quality according to (19), wherein proline 3-hydroxylase or proline 4-hydroxylase gene derived from a microorganism belonging to a genus selected from the group consisting of the generaAmycolatopsis, Dactylosporangium and Streptomyces is introduced into the microorganism.

(21) The method of inhibiting skin aging and/or improving skin quality according to any one of (15) to (20), wherein said method of inhibiting skin aging and/or improving skin quality is a method of promoting the proliferation of epidermal cells.

(22) The method of inhibiting skin aging and/or improving skin quality according to any one of (15) to (20), wherein said method of inhibiting skin aging and/or improving skin quality is a method of promoting the collagen synthesis of fibroblast.

(23) The method of inhibiting skin aging and/or improving skin quality according to any one of (15) to (20), wherein said method of inhibiting skin aging and/or improving skin quality is a method of improving the moisture retention function of epidermis.

(24) The method of inhibiting skin aging and/or improving skin quality according to any one of (15) to (20), wherein said method of inhibiting skin aging and/or improving skin quality is a method of inhibiting and/or improving the wrinkle formation.

(25) The method of inhibiting skin aging and/or improving skin quality according to any one of (15) to (24), wherein said skin is human skin.

(26) A method of inhibiting skin aging and/or improving skin quality, which comprises applying onto skin a cosmetic composition for inhibiting skin aging and/or skin quality-improving, the cosmetic composition containing hydroxyproline, its N-acyl derivatives or salts thereof.

(27) The method of inhibiting skin aging and/or improving skin quality according to (26), wherein said cosmetic composition contains 0.01–5 wt % of hydroxyproline, N-acylated hydroxyproline derivatives or salts thereof based on the total wight.

(28) The method of inhibiting skin aging and/or improving skin quality according to (26) or (27), wherein said N-acylated hydroxyproline derivatives are N-acetylated hydroxyproline derivatives or N-proionated hydroxyproline derivatives.

(29) The method of inhibiting skin aging and/or improving skin quality according to any one of (26) to (28), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(30) The method of inhibiting skin aging and/or improving skin quality according to any one of (26) to (29), wherein said hydroxyproline is produced by using a microorganism.

(31) The method of inhibiting skin aging and/or improving skin quality according to (30), wherein proline 3-hydroxylase or proline 4-hydroxylase gene derived from a microorganism belonging to a genus selected from the group consisting of the generaAmycolatopsis, Dactylosporangium and Streptomyces is introduced into the microorganism.

(32) The method of inhibiting skin aging and/or improving skin quality according to any one of (26) to (31), wherein said method of inhibiting skin aging and/or improving skin quality is a method of promoting the proliferation of epidermal cells.

(33) The method of inhibiting skin aging and/or improving skin quality according to any one of (26) to (31), wherein said method of inhibiting skin aging and/or improving skin quality is a method of promoting the collagen synthesis of fibroblast.

(34) The method of inhibiting skin aging and/or improving skin quality according to any one of (26) to (31), wherein said method of inhibiting skin aging and/or improving skin quality is a method of improving the moisture retention function of epidermis.

(35) The method of inhibiting skin aging and/or improving skin quality according to any one of (26) to (31), wherein said method of inhibiting skin aging and/or improving skin quality is a method of inhibiting and/or improving the wrinkle formation.

(36) The method of inhibiting skin aging and/or improving skin quality according to any one of (26) to (35), wherein said skin is human skin.

(37) Use of hydroxyproline, N-acylated hydroxyproline derivatives or salts thereof for producing skin aging inhibitors and/or skin quality-improving agents.

(38) The use according to (37), wherein said skin aging inhibitors and/or skin quality-improving agents contain 0.01 to 5 wt % of hydroxyproline, N-acylated hydroxyproline derivatives or salts thereof based on the total weight.

(39) The use according to (37) or (38), wherein said N-acylated hydroxyproline derivatives are N-acetylated hydroxyproline derivatives or N-propionated hydroxyproline derivatives.

(40) The use according to any one of (37) to (39), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(41) The use according to any one of (37) to (40), wherein said hydroxyproline is produced by using a microorganism.

(42) The use according to (41), wherein proline 3-hydroxylase or proline 4-hydroxylase gene derived from a microorganism belonging to a genus selected from the group consisting of the generaAmycolatopsis, Dactylosporangium and Streptomyces is introduced into the microorganism.

(43) The use according to any one of (37) to (42), wherein said skin aging inhibitors and/or skin quality-improving agents are agents for promoting the epidermal cells.

(44) The use according to any one of (37) to (42), wherein said skin aging inhibitors and/or skin quality-improving agents are agents for promoting the collagen synthesis of fibroblast.

(45) The use according to any one of (37) to (42), wherein said skin aging inhibitors and/or skin quality-improving agents are agents for improving the moisture retention function of epidermis.

(46) The use according to any one of (37) to (42), wherein said skin aging inhibitors and/or skin quality-improving agents are agents for improving and/or inhibiting the wrinkle formation.

(47) The use according to any one of (37) to (46), wherein said skin is human skin.

(48) Use of hydroxyproline, N-acylated hydroxyproline derivatives or salts thereof for producing a cosmetic composition for skin aging inhibition and/or skin quality improvement.

(49) The use according to (48), wherein said cosmetic composition contains 0.01 to 5 wt % of hydroxyproline, its N-acylated hydroxyproline derivatives or salts thereof based on the total weight.

(50) The use according to (48) or (49), wherein said N-acylated hydroxyproline derivatives are N-acetylated hydroxyproline derivatives or N-propionated hydroxyproline derivatives.

(51) The use according to any one of (48) to (50), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(52) The use according to any one of (48) to (51), wherein said hydroxyproline is produced by using a microorganism.

(53) The use according to (52), wherein proline 3-hydroxylase or proline 4-hydroxylase gene derived from a microorganism belonging to a genus selected from the group consisting of the generaAmycolatopsis, Dactylosporangium and Streptomyces is introduced into the microorganism.

(54) The use according to any one of (48) to (53), wherein the skin aging inhibition and/or skin quality improvement is promotion of the proliferation of epidermal cells.

(55) The use according to any one of (48) to (53), wherein the skin aging inhibition and/or skin quality improvement is promotion of the collagen synthesis of fibroblast.

(56) The use according to any one of (48) to (53), wherein the skin aging inhibition and/or skin quality improvement is improvement of the moisture retention function of epidermal cells.

(57) The use according to any one of (48) to (53), wherein the skin aging inhibition and/or skin quality improvement is inhibition and/or improvement of the wrinkle formation.

(58) The use according to any one of (48) to (57), wherein said skin is human skin.

(59) Use of hydroxyproline, N-acylated hydroxyproline derivatives or salts thereof for skin aging inhibition and/or skin quality improvement.

(60) The use according to (59), wherein said N-acylated hydroxyproline derivatives are N-acetylated hydroxyproline derivatives or N-propionated hydroxyproline derivatives.

(61) The use according to (59) or (60), wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

(62) The use according to any one of (59) to (61), wherein said hydroxyproline is produced by using a microorganism.

(63) The use according to (62), wherein proline 3-hydroxylase or proline 4-hydroxylase gene derived from a microorganism belonging to a genus selected from the group consisting of the generaAmycolatopsis, Dactylosporangium and Streptomyces is introduced into the microorganism.

(64) The use according to any one of (59) to (63), wherein said skin aging inhibitors and/or skin quality-improving agents are agents for promoting the proliferation of epidermal cells.

(65) The use according to any one of (59) to (63), wherein said skin aging inhibitors and/or skin quality-improving agents are agents for promoting the collagen synthesis of fibroblast.

(66) The use according to any one of (59) to (63), wherein said skin aging inhibitors and/or skin quality-improving agents are agents for improving the moisture retention function of epidermis.

(67) The use according to any one of (59) to (63), wherein said skin aging inhibitors and/or skin quality-improving agents are agents for inhibiting and/or improving the wrinkle formation.

(68) The use according to any one of (59) to (67), wherein said skin is human skin.

The skin aging inhibitor and/or skin quality-improving agent in the present invention mean substance having either skin aging inhibiting activity or skin quality-improving activity or substance having both of the skin aging inhibiting activity and skin quality-improving activity.

The hydroxyproline to be used in the present invention includes any one of 8 kinds of stereoisomers in which the proline may take any of D-form or L-form, the hydroxyl group may be located at the 3-position or the 4-position, and the stereoisomer may take any of the cis-form or the trans-form.

Examples of hydroxyproline includes cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

Hydroxyproline is a kind of amino acid broadly existing in the nature as a major amino acid component of collagen and also as one of amino acids composing elastin, and can be prepared by acid hydrolysis of collagen derived from animals such as pig, cow, etc. and purifying it according to a conventional method.

Trans-4-hydroxy-L-proline can be prepared by using proline 4-hydroxylase isolated from genus Amycolatopsis or genus Dactylosporangium. (JP, 7-313179, A). Further, cis-3-hydroxy-L-proline can be prepared by using proline 3-hydroxylase (JP, 7-322885, A) isolated from genus Streptomyces [Bioindustry, 14, 31 (1997)].

In the present invention, hydroxyproline produced by using microorganisms is preferable, because the product in high quality is easily available.

N-acyl derivative of hydroxyproline to be used in the present invention includes those N-acyl derivatives of various hydroxyproline stereoisomers as described above. The acyl group of said N-acyl derivative is not particularly limited, however, preferred is acyl group having 1–24 carbon atoms, more preferred is acyl group having 1–12 carbon atoms and particularly preferred is acyl group having 1–6 carbon atoms. Examples of the acyl group are formyl, acetyl, propionyl, butyryl, isobutyryl, valeryl, pivaloyl, hexanoyl, heptanoyl, octanoyl, nonanoyl, decanoyl, undecanoyl, dodecanoyl, and the like.

The salt of the hydroxyproline or hydroxyproline N-acyl derivative includes salts of alkali metal such as sodium, potassium, lithium, etc., salts of alkaline earth metal such as calcium, magnesium, etc., ammonium salt, salts of amines such as monoethanolamine, diethanolamine, triethanolamine, triisopropanolamine, etc., and salts of basic amino acids such as arginine, lysine, etc.

The N-acyl derivative of hydroxyproline can be prepared in a conventional method. For example, N-acyl derivative of hydroxyproline can be prepared by reacting a straight-chain or branched, saturated or unsaturated fatty acid having 1–24 carbon atoms with halogenating agent such as thionyl chloride and phosgene to give the halide such as chloride and bromide, and condensing the halide with said hydroxyproline, or the N-acyl derivative can be prepared by converting said fatty acid into the acid anhydride and reacting the acid anhydride with hydroxyproline.

As the fatty acid, formic acid, acetic acid, propionic acid, butyric acid, isobutyric acid, valeric acid, isovaleric acid, pivalic acid, hexanoic acid, heptanoic acid, octanoic acid, nonanoic acid, decanoic acid, undecanoic acid, dodecanoic acid, etc., may be used singly or in combination.

The method of producing N-acylated hydroxyproline derivative via acid halide will be shown below.

Fatty acid is dispersed in a solvent such as methylene chloride, chloroform, carbon tetrachloride, benzene, toluene, xylene or n-hexane, and 1–5 equivalent of halogenating agent is added thereto for reaction, whereby a fatty acid halide is obtained. Then, hydroxyproline is added or dispersed in a solvent, and the acylation reaction is carried out by adding fatty acid halide thereto in an amount of 0.3 to 3.0 equivalents based on hydroxy proline while keeping the temperature of the resultant mixture at 5–70° C., and the N-acylated hydroxyproline derivatives.

As the solvent to be used for the acylation reaction, water, methanol, ethanol, isopropanol, isobutanol, acetone, toluene, tetrahydrofuran, ethyl acetate, N,N-dimethylformamide, dimethylsulfoxide, etc., may be used singly or in combination. At the time of dissolving or dispersing hydroxyproline in a solvent, alkali materials such as sodium hydroxide, potassium hydroxide, etc., may be dissolved or dispersed in the solvent in an amount of 0.8 to 2.0 equivalents based on hydroxyproline, if necessary.

When a salt of N-acylated hydroxyproline is desired, and the N-acylated hydroxyproline derivative would be obtained in the form of the desired salt, the salt may be purified as it is. If the product is obtained in the free state, and its salt is desired, it may be dissolved or suspended in an appropriate solvent, followed by addition of a base to form a salt.

Purification may be carried out in a conventional manner such as crystallization, chromatography, or the like.

In the skin aging inhibitors and/or skin quality-improving agents as well as cosmetic composition for inhibiting the skin aging and/or improving skin quality of the present invention, hydroxyproline such as cis/trans-4-hydroxy-L/D-proline, cis/trans-3-hydroxy-L/D-proline, N-acylated hydroxyproline derivatives or salts thereof can be used singly or in combination.

The content of hydroxyproline, N-acylated hydroxyproline derivatives or salts thereof in the skin aging inhibitors and/or skin quality-improving agents and in cosmetic composition of the present invention may vary in a wide range depending on the desired effect. For example, the content of these compounds in the skin aging inhibitors and/or skin quality-improving agents and in said cosmetic composition is 0.01 to 5 wt %, preferably 0.1 to 5 wt %, more preferably 0.5 to 3 wt %.

In the present invention, as the skin aging inhibiting activity and/or skin quality-improving activity, the activity for promoting the proliferation of epidermal cells, the activity for promoting collagen synthesis of fibroblast, the activity for improving moisture retention function of epidermis, the activity for inhibiting and/or improving wrinkle formation, etc. are mentioned, however, the activities are not limited thereto. Further, the cosmetic composition of the present invention is used for skin of pet animal such as mouse, dog, cat, horse, etc., and human skin, and preferably used for human skin.

As an agent for promoting the fibroblast collagen synthesis or an agent for improving moisture retention function of epidermis, N-acylated hydroxyproline derivative is preferable, and N-acetylhydroxyproline is more preferable.

The skin aging inhibitors and/or skin quality-improving agents, and the cosmetic composition for inhibiting skin aging and/or improving skin quality of the present invention containing the skin aging inhibitors and/or skin quality-improving agents of the present invention may ccontain conventional ingredients to be used for ordinary cosmetics, if necessary, in addtion to said essential ingredients.

Examples of said conventional ingredients are solid oil, semi-solid oils, other moisturizers, emollients, water soluble polymers, oil soluble polymers, various surfactants, inorganic or organic pigments, inorganic or organic pigments treated with silicone or fluorine compounds, coloring agents such as organic dyestuffs, etc., ethanol, ultraviolet ray absorbents, antiseptics, antioxidants, pigments, thickeners, pH regulators, perfumes, blood circulation promoters, coolsensitive agents, antiperspirants, fungicides, skin softers, water, and so on. Those ingredients may be added within the qualitative or quantitative range in which the object and effect of the present invention are not damaged.

Examples of the solid oil or semi-solid oil are vaseline, lanolin, ceresin, microcrystalline wax, carnauba wax, candelilla wax; higher fatty acids such as coconut oil fatty acids, lauric acid, or hardened beef tallow fatty acids, etc.; and higher alcohols such as lauryl alcohol, cetyl alcohol, stearyl alcohol, or behenyl alcohol, etc.

Examples of the liquid oil are vegetable oil such as avocado oil and olive oil; fatty acid such as oleic acid and isostearic acid.; alcohols such as hexadecyl alcohol and oleyl alcohol; ester oil such as cetyl 2-ethylhexanoate, 2-octyldodecyl myristate, neopentyl glycol di-2-ethylhexanoate, glycerol tri-2-ethylhexanoate, 2-octyldodecyl oleate, isopropyl myristate, glycerol triisostearate, diglyceride 2-ethylhexanoate and long-chain acylglutaminic acid octyldodecyl ester; silicone oil such as dimethylpolysiloxane, methyl-hydrogenpolysiloxane, methylphenylpolysiloxane, octamethyl-cyclotetrasiloxane, etc.; liquid hydrocarbon oil such as liquid paraffin, squalene, squalane, etc.

Examples of the moisturizer are lipophilic moisturizer, low molecular moisturizer, and high molecular moisturizer.

Examples of the lipophylic moisturizer are lysolecithin, lecithin, cholesterol, cholesterol esters, sphingolipids, ceramides, and so on.

Examples of the low molecular moisturizer are serine, glutamine, sorbitol, mannitol, glycerin, sodium pyrrolidonecarboxylate, 1,3-butylene glycol, propylene glycol, lactic acid, lactic acid salts, and the like.

Examples of the high molecular moisturizer are hyaluronic acid, sodium hyaluronate, elastin, alginic acid, mucopolysacchrides, polyethylene glycol, polyaspartic acid salts, water soluble chitin, and so on.

Examples of the emollient are long-chain acylglutamic acid cholestcryl esters, cholesteryl hydroxystearate, 12-hydroxystearic acid, stearic acid, rhodinic acid, lanolin fatty acid cholesteryl ester, and so on.

Examples of the surfactant are non-ionic surfactant such as polyoxyethylene (hereinafter referred to as "POE") cetyl ether, POE stearic acid ester, POE sorbitan monolaurate, glycerin fatty acid ester, polyglycerin fatty acid ester and polyoxyethylene hardened castor oil; cationic surfactants such as benzalkonium chloride, stearyltrimethylammonium chloride, dicetyldimethylammonium chloride and behenyltrimethylammonium chloride; amphoteric surfactant such as 2-cocoyl-N-carboxymethyl-N-hydroxyethyl-imidazolinium betaine and betaine amidoacetate; and anionic surfactant such as higher alcohol sulfates, higher alcohol ether sulfates, long-chain fatty acid alkali metal salts, long-chain fatty acid alkali earth metal salts, long-chain fatty acid basic amino acid salts, N-long-chain acylamino acids and N-long-chain acylamino acid salts.

Examples of the water soluble polymer are water soluble polymers frequently used for cosmetics such as carboxymethyl cellulose, methyl cellulose, hydroxymethyl cellulose, polyvinyl alcohol, polyvinylpyrrolidone, tragacanth gum, carrageenan, dextrin, dextrin fatty acid ester, carboxyvinyl polymer, xanthan gum, gelatin, sodium alginate and arabic gum.

Examples of the oil soluble polymer are oil soluble polymers frequently used for cosmetics such as polyvinylpyrrolidone cicosene copolymers, polyvinylpyrrolidone hexadecene copolymers, nitrocellulose and high molecular silicones.

Examples of organic or inorganic pigment are inorganic powder such as silic acid, anhydrous silic acid, magnesium silicate, talc, sericite, mica, kaolin, red iron oxide, clay, bentonite, titanium coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine blue, chromium oxide, chromium hydroxide, calamine and carbon black, and complex thereof; etc.; organic powder such as polyamide, polyester, polypropylene, polystyrene, polyurethane, vinyl resins, urea resins, phenol resins, fluorine resins, silicon resins, acryl resins, melamine resins, epoxy resins, polycarbonate resins, divinylbenzene-styrene copolymers, silk powder, cellulose, CI pigment yellow and CI pigment orange, and complex of the inorganic powder and organic powder mentioned above.

Examples of the organic powder are metallic soap such as calcium stearate; alkylphosphoric acid polyvalent metal salts such as zinc sodium cetylphosphate, zinc laurylphosphate and calcium laurylphosphate; acylamino acid polyvalent metal salts such as N-lauroyl-β-alanine calcium, N-lauroyl-β-alanine zinc and N-lauroylglycine calcium; amidosulfonic acid polyvalent metal salts such as N-lauroyl-taurine calcium and N-palmitoyl-taurine calcium; basic N-acylamino acid such as $N^{\epsilon}$-lauroyl-L-lysine, $N^{\epsilon}$-palmitoyllysine, $N^{\alpha}$-palmitoylornithine, $N^{\alpha}$-lauroylarginine and $N^{\alpha}$-hardened beef tallow fatty acid acylarginine; N-acylpolypeptides such as N-lauroylglycylglycine; α-amino fatty acids such as α-aminocaprylic acid and α-aminolauric acid; and resin powders such as polyethylene, polypropylene, nylon, polymethyl methacrylate, polystyrene, divinylbenzene-styrene copolymers and ethylene tetrafluoride.

Examples of the ultraviolet ray absorbent are p-aminobenzoic acid and p-aminobenzoic acid derivatives such as octyl p-dimethylaminobenzoate; benzophenone derivatives such as 2-hydroxy-4-methoxybenzophenone and dihydroxydimethoxybenzophenone; methoxycinnamic acid derivatives such as ethyl p-methoxycinnamate and octyl p-methoxycinnamate; salicylic acid derivatives such as octyl salicylate and homomenthyl salicylate; α-dehydroamino acid derivatives such as N-benzoyl-O-methyl-α-dehydrothyrosine 2-ethylhexyl ester.; benzal hydantoin derivatives such as 2-ethylhexyl 4-(3-,4-dimethoxypheny) methylene-2,5-dioxo-1-imidazolidinepropionate; urocanic acid, ethyl urocanate, 4-tert-butyl-4'-methoxydibenzoylmethane, 2-(2'-hydroxy-5'-methylphenyl)-benzotriazole, etc.

Examples of the antiseptic are methylparabene, and so on.

Examples of the skin softener are liquid paraffin, vaselin, olive oil, squalane, lanolin, synthetic ester oil, and so on.

Any ingredients mentioned above may be used within the range in which the object and effect of the present invention are not damaged, and its content is preferably 0.01 to 5 wt %, and more preferably 0.01 to 3 wt %.

Agents as well as cosmetic compositions for inhibiting the skin aging and/or improving skin quality, promoting the epidermis proliferation, promoting the fibroblast collagen synthesis, improving the moisture retention function of epidermis, or inhibiting and/or improving the wrinkle formation, etc. in the present invention may take the forms such as solution, emulsion, paste mixture or the like.

As the cosmetic compositions for inhibiting the skin aging and/or improving skin quality containing the skin aging inhibitors and/or skin quality-improving agents of the present invention, mentioned are facial cleansing cream, facial cleansing foam, cleansing cream, cleansing milk, cleansing lotion, massage cream, cold cream, moisture cream, emulsion, cosmetic lotion, pack, after shaving cream, sun screen cream, suntan oil, body shampoo, hair shampoo, hair rinse, hair treatment, hair tonic, hair restoration, stick pomade, hair cream, hair liquid, set lotion, hair spray, hair dye, color rinse, color spray, permanent wave liquid, press powder, loose powder, eye shadow, or hand cream, etc.

The skin aging inhibitors and/or skin quality-improving agents as well as cosmetic composition for inhibiting the skin aging and/or improving skin quality containing said skin aging inhibitors and/or skin quality-improving agents may take a formulation such as emulsion, cream, face lotion, pack, foundation and hair cosmetic without specific limitation.

Method of using the skin aging inhibitors and/or skin quality-improving agents as well as cosmetic compositions for inhibiting the skin aging and/or improving skin quality containing said skin aging inhibitors and/or skin quality-improving agents vary depending upon the age, individual and part of body to be used. Appropriate concentration of hydroxyproline, N-acylated hydroxyproline derivatives or salts thereof in the cosmetic composition is preferably 0.01 to 5 wt %, preferably 0.1 to 5 wt %, more preferably 0.5 to 3 wt %, and it is recommended to apply the cosmetic composition onto the skin once to several times per day in an amount of 0.1–5 μl, preferably 1–5 μl, and more preferably 2 μl, however, the application is not limited to the recommended one.

Certain embodiments of the present invention will be illustrated in the following examples, which should not be construed as limiting the invention thereto.

BEST MODE FOR CARRING OUT THE INVENTION

EXAMPLE 1

Preparation of a Cosmetic Composition Containing trans-4-hydroxy-L-proline

To purified water were added 0.5 wt % of trans-4-hydroxy-L-proline (hereinafter referred to as "Hyp", manufactured by Kyowa Hakko Kogyo Co., Ltd.), 0.1 wt % of methylparaben and 0.17 wt % of glycerol, and the resultant mixture was melted to give a cosmetic composition containing Hyp (Composition 1).

EXAMPLE 2

Preparation of a Cosmetic Composition Containing trans-4-hydroxy-L-proline

To purified water were added 3 wt % of Hyp, 0.1 wt % of methylparaben and 0.17 wt % of glycerol, and the resultant mixture was melted to give a cosmetic composition containing Hyp (Composition 2).

EXAMPLE 3

Preparation of a Cosmetic Composition Containing N-acetyl-trans-4-hydroxy-L-proline To purified water were added 3 wt % of N-acetyl-trans-4-hydroxy-L-proline (hereinafter optionally referred to as "N-Acetyl-Hyp"), 0.1 wt % of methylparaben and 0.17 wt % of glycerol, and the resultant mixture was melted to give a cosmetic composition containing N-Acetyl-Hyp manufactured by Kyowa Hakko Kogyo Co., Ltd. (Composition 3).

EXAMPLE 4

Preparation of a Cosmetic Composition Containing Collagen

To purified water were added 1 wt % of collagen (Collagen CLR, manufactured by Kotobuki Chemical), 0.1 wt % of methylparaben and 0.17 wt % of glycerol, and the resultant mixture was melted to give a cosmetic composition containing collagen (Composition 4).

EXAMPLE 5

Preparation of a Cosmetic Composition Containing trans-4-hydroxy-L-proline and Lecithin To purified water were added 0.5 wt % of Hyp, 0.05 wt % of lecithin (SLP-White H, manufactured by True Lecithin Kogyo), 0.01 wt % of hyaluronic acid (Hyaluronic Acid LP, manufactured by Kyowa Hakko Kogyo Co., Ltd.), 0.1 wt % of methylparaben and 0.17 wt % of glycerol, and the resultant mixture was melted to give a cosmetic composition containing Hyp and lecithin (Composition 5).

EXAMPLE 6

Preparation of a Cosmetic Composition Containing trans-4-hydroxy-L-proline and Lysolecithin:n To purified water were added 3 wt % of Hyp, 0.05 wt % of lysolecithin (Lysolecithin Kyowa, manufactured by Kyowa Hakko Kogyo Co., Ltd.), 0.01 wt % of hyaluronic acid (Hyaluronic Acid LP, manufactured by Kyowa Hakko Kogyo Co., Ltd.), 0.1 wt % of methylparaben and 0.17 wt % of glycerol, and the resultant mixture was melted to give a cosmetic composition containing Hyp and lysolecithin (Composition 6).

EXAMPLE 7

Preparation of a Cosmetic Composition Containing trans-4-hydroxy-L-proline and Lecithin To purified water were added 3 wt % of Hyp, 0.05 wt % of lecithin (PC92H, manufactured by True Lecithin Kogyo), 0.01 wt % of hyaluronic acid (Hyaluronic Acid LP, manufactured by Kyowa Hakko Kogyo Co., Ltd.), 0.01 wt % of methylparaben and 0.17 wt % of glycerol, and the resultant mixture was melted to give a cosmetic composition containing Hyp and lecithin (Composition 7).

EXAMPLE 8

Preparation of a Cosmetic Composition Containing trans-4-hydroxy-L-proline and Lecithin To purified water were added 3 wt % of Hyp, 0.05 wt % of lecithin (SLP-White H, manufactured by True Lecithin Kogyo), 0.01 wt % of hyaluronic acid (Hyaluronic Acid LP, manufactured by Kyowa Hakko Kogyo Co., Ltd.), 0.1 wt % of methylparaben and 0.17 wt % of glycerol, and the resultant mixture was melted to give a cosmetic composition containing Hyp and lecithin (Composition 8).

The composition of the cosmetic compositions in Examples 1–8 are collectively shown in Table 1.

TABLE 1

| Ingredient (% by weight) | Composition of Cosmetic Compositions Cosmetic Composition | | | | | | | |
|---|---|---|---|---|---|---|---|---|
| | (1) | (2) | (3) | (4) | (5) | (6) | (7) | (8) |
| Hyp | 0.5 | 3 | — | — | 0.5 | 3 | 3 | 3 |
| N-Acetyl-Hyp | — | — | 3 | — | — | — | — | — |
| Collagen | — | — | — | 1 | — | — | — | — |
| Lecithin SLP | — | — | — | — | 0.05 | — | — | 0.05 |
| Lecithin PC92 | — | — | — | — | — | — | 0.05 | — |
| Lysolecithin | — | — | — | — | — | 0.05 | — | — |
| Hyaluronic acid | — | — | — | — | 0.01 | 0.01 | 0.01 | 0.01 |
| Methylparaben | 0.1 | 0.1 | 0.1 | 0.1 | 0.1 | 0.1 | 0.1 | 0.1 |
| Glycerol | 0.17 | 0.17 | 0.17 | 0.17 | 0.17 | 0.17 | 0.17 | 0.17 |

Hyp: trans-4-hydroxy-L-proline
N-Acetyl-Hyp: N-acetyl-trans-4-hydroxy-L-proline
Lecithin SLP: Lecithin (SLP-White H, manufactured by True Lecithin Kogyo Co., Ltd.)
Lecithin PC92: Lecithin (PC92H, manufactured by True Lecithin Kogyo Co., Ltd.)

EXAMPLE 9

Collagen Synthesis Promotion Activity in Human Fibroblast

Assay of synthetic collagen was conducted by the following method according to "Experimental Method of Collagen" (Written by Nagai, et al., Kodansha Scientific).

Fibroblast derived from human neonate (Sanko Junyaku Co., Ltd.) was cultivated in DMEM medium [Virology, 8, 396 (1959)] containing 10% fetal bovine serum under conditions of 5% $CO_2$ at 37° C. by the stationary phase. $^3$H marked glycine and a test compound was added thereto, and further cultivated for 72 hours. DMEM medium was prepared by mixing Dulbecco's Modified Eagle's Medium "Nissui" (2) (manufactured by Nissui Pharmaceutical) with 4 mmol/L glutamine, an optimum dose of sodium hydrogencarbonate, 10 mmol/L HEPES, 50 U/ml penicillin G potassium, 50 µg/ml streptomycin and 10% fetal bovine serum.

To the resultant culture broth was added 500 µmol/L phenylmethanesulfonyl fluoride (PMSF), and the cells and medium were recovered, crashed with a sonicater and the protein was extracted.

To the extract were added 100 µmol/L bovine serum albumin (BSA) and 10% trichloroacetic acid (TCA), and the resultant mixture was centrifuged at 3000 rpm for 5 minutes to recover the precipitate.

To the precipitate was added 0.2 mol/L sodium hydroxide at a density of 8 µl per 1 $cm^2$ of the bottom area of culture vessel used for said cultivation, and the resultant mixture was neutralized with an equivalent amount of 1 mol/L phosphate buffer.

To 100 µl of the resultant protein solution were added 25 mmol/L calcium chloride (10 µmol/L), 62.5 mmol/L N-ethylmaleimide (20 µmol/L) and 20 units of collagenase (manufactured by Wako Pure Chemical Industries, Ltd.; for analyzing the collagen), and the resultant mixture was allowed to react at 37° C. for 90 minutes.

The reaction mixture was filtered with an ultrafilter (molecular weight: 10,000), and the protein fraction of the filtrate was subjected to radiation activity (CDP) assay, which was assigned as freshly prepared collagen. The radiation activity (NCDP) of the non-filtered protein fraction was assayed, and collagen synthetic ratio was calculated according to the following formula 1.

Relative collagen synthetic promotion activity (change in the collagen synthesis) was calculated according to the following formula 2, comparing with the relative value of the collagen synthetic ratio of the test compounds against control.

$$\text{Collagen Synthetic Ratio} = \frac{CDP}{CDP + NCDP} \quad \text{(Formula 1)}$$

$$\text{Relative Collagen Synthetic Promotion Activity}(\%) = \quad \text{(Formula 2)}$$
$$\frac{\text{Collagen Synthetic Ratio of Test Compound}}{\text{Collagen Synthetic Ratio of Control}} \times 100$$

The result was shown in Table 2.

Collagen synthetic promotion activity was observed in Hyp and N-Acetyl-Hyp.

TABLE 2

| | Collagen Synthetic Promotion Activity. | | |
|---|---|---|---|
| Test Compound | 0 mM | 0.1 mM | 1 mM |
| Hyp | 100 | 108.3 | 117.1 |
| N-Acetyl-Hyp | 100 | 121.1 | 119.7 |

EXAMPLE 10

Human Epidermal Cell Proliferation Activity

The human epidermal cell proliferation activity was assayed according to MTT method [Cell Culture III, 4477–4482 (1984)] by incorporating 3-(4,5-dimethylthiazol-2-yl)-2,5-diphenyltetrazolium bromide (MTT) into cells and measuring the resultant MTT formazan by colorimetry at the wave length of 570 nm (Reference, 650 nm).

That is, epidermal keratinized cells derived from human neonate (Sanko Junyaku Co., Ltd.) was cultivated in KGM medium (Sanko Junyaku Co., Ltd.) in an atmosphere of 5% $CO_2$ at 37° C. by the stationary phase, mixed with Hyp and N-Acetyl-Hyp and cultivated for 4 days. Then, the culture broth was mixed with 1/10 volume of 5 mg/ml MTT reagent in a phosphate buffer (pH 7.4, free of calcium and magnesium), and cultivated in an atmosphere of 5% $CO_2$ at 37° C. for 4 hours. After removing the medium, MTT formazan in the cell was extracted with isopropanol containing 0.4 mol/L hydrochloric acid, and the absorbance at 570 nm was measured in comparison with that of 630 nm.

The result was shown in Table 3.

Epidermal cells proliferation activity was observed in Hyp and N-Acetyl-Hyp. Proliferation activity depending on the concentration was found in Hyp.

TABLE 3

Epidermal Cell Proliferation Activity

| Test compound | 0 mM | 10 mM | 100 mM |
|---|---|---|---|
| Hyp | 100 | 111.6 | 135.1 |
| N-Acetyl-Hyp | 100 | 108.7 | 85.9 |

EXAMPLE 11

Mouse Epidermal Cell Proliferation Activity

Epidermis was peeled from 3 days old C3H mouse according to Method of Tanigaki, et al., [The Japanese Journal of Dermatology, 1145–1152 (1989)].

The epidermis was treated with 0.25% trypsin and centrifuged at 1500 rpm for 5 minutes to obtain the cells. The cells were inoculated onto DMEM medium containing 10% fetal bovine serum and cultivated at 37° C. for 1 day to give the mouse epidermal cells.

The mouse epidermal cells were cultivated on MCDB 153 medium free of serum containing the test compound (Hyp or N-Acetyl-Hyp) for 6 days, mixed with 1/10 volume of 5 mg/ml MTT reagent in phosphate buffer (pH 7.4, free of calcium and magnesium), and then cultivated in an atmosphere of 5% $CO_2$ at 37° C. for 4 hours. After removing the medium, MTT formazan in the cell was extracted with isopropanol containing 0.4 mol/L hydrochloric acid, and the absorbance at 570 nm was measured in comparison with that of 630 nm. The result was shown in Table 4.

Epidermal proliferation activity was found in Hyp and N-Acetyl-Hyp.

TABLE 4

Epidermal Cell Proliferation Activity:

| Test compound | 0 µM | 1 µM | 3 µM | 10 µM |
|---|---|---|---|---|
| Hyp | 100 | 88.6 | 107.5 | 126 |
| N-Acetyl-Hyp | 100 | 110.7 | 118.2 | 121.9 |

EXAMPLE 12

Evaluation of Moisture Retention Function (1)

Change in the moisture retention function by continuous use was examined for the evaluation of the skin quality-improving effect of Compositions (1)–(8) prepared in Examples 1–8.

(Test Method)

The compositions are applied to the test part/cubital fossa of 4 healthy female panelists in 23–28 years old in an amount of 2 µl/cm² twice a day in the morning and evening for 3 weeks or 2 months.

(Evaluation Method)

Moisture content in the test part before the application of the cosmetic composition was measured in the morning with the elapse of time. The probe was contacted vertically on the test part, and the skin conductivity (=moisture content) was assayed with SKICON-200 (manufactured by IBS) as a measuring machine.

When the measured value is high, it means that the moisture content is high. Change in the skin conductivity (relative conductivity) on the test part was calculated according to the following formula 3, as a relative value to the change in the conductivity on the non-treated part.

$$\text{Relative Conductivity}(\%) = \frac{\text{Daily Conductivity of the Test Part}}{\text{Conductivity of the Test Part on day 0}} \div \frac{\text{Daily Conductivity of the Non-treated Part}}{\text{Conductivity of the Test Part on day 0}} \times 100 \quad \text{(Formula 3)}$$

The results were shown in Tables 5-1 and 5-2.

Skin moisture content was enhanced by continuous application of each of test composition, and accordingly, an improvement in the moisture retention function was observed in Hyp and N-Acetyl-Hyp. Further, an improving effect exceeding that of collagen was observed in N-Acetyl-Hyp.

TABLE 5-1

Improvement in the Moisture Retention Function:

| | Relative Conductivity (%) | | | | |
|---|---|---|---|---|---|
| Test Composition | Day 0 | Day 14 | Day 28 | Day 42 | Day 56 |
| Purified Water | 100 | 96.9 | 94.5 | 88.7 | 93.8 |
| Composition (1) | 100 | 125.2 | 119.8 | 111.1 | 109.6 |
| Composition (2) | 100 | 127.5 | 118.2 | 108.6 | 110.3 |
| Composition (3) | 100 | 238.2 | 226.9 | 233.5 | 186.3 |
| Composition (4) | 100 | 133.3 | 134.5 | 130.8 | 121.5 |
| Composition (5) | 100 | 157.8 | 124.6 | 132.4 | 127 |

TABLE 5-2

Improvement in the Moisture Retention Function

| | Relative Conductivity (%) | | | | |
|---|---|---|---|---|---|
| Test Composition | Day 0 | Day 5 | Day 9 | Day 16 | Day 21 |
| Purified Water | 100 | 96.9 | 94.5 | 88.7 | 93.8 |
| Composition (4) | 100 | 104.3 | 129.9 | 115.3 | 136.8 |
| Composition (6) | 100 | 120.9 | 144.3 | 140.6 | 172 |
| Composition (7) | 100 | 108.3 | 150.2 | 123.3 | 145.2 |
| Composition (8) | 100 | 117 | 145.7 | 185.9 | 146.1 |

EXAMPLE 13

Evaluation of Moisture Retention Function (2)

Concentration dependency on moisture retention effect of N-Acetyl-Hyp was evaluated by the single application.

(Test Method)

The moisture retention was assayed on the test part/cubital fossa of 12 healthy female panelists in 23–32 years old, and each of the test compositions was applied thereto in an amount of 2 μl/cm² and allowed to leave.

Three hours later, the moisture content of the test part was measured, and the moisture retention effect was evaluated in terms of the relative conductivity when the moisture content before the application was defined as 100%.

The result was shown in Table 6. N-Acetyl-Hyp exhibited concentration dependent-moisture retention effect even by single treatment.

TABLE 6

Moisture Retention Function of N-Acetyl-Hyp:

| | Purified water | N-Acetyl-Hyp | | | |
|---|---|---|---|---|---|
| | | 1% | 3% | 5% | 10% |
| Relative Conductivity (%) | 91 | 100 | 129 | 186 | 189 |

EXAMPLE 14

Skin Quality-improving Effect

Silicone replica on the test part of the panelists were prepared using "Skin Cast" [trademark, manufactured by Yamada Shogyo] during the test in Example 12, and the skin condition was scored for evaluation of the skin quality-improving effect according to the following criteria.

Score of the Skin Condition
Score 1
  Skin furrows are unclear, but peeled keratin is seen.
Score 2
  Skin furrows are slightly unclear or directional tendency.
Score 3
  Skin furrows are seen, but shallow or directional tendency.
Score 4
  Skin furrows are seen or slight meshy.
Score 5
  Skin furrows are clearly seen or clearly meshy.

The result are shown in Table 7. The scores of Compositions (1)–(5) increased by 0.4–2.1 improvement in comparison with the purified water, which proved clearly skin quality. That is, the skin become smooth, and wrinkle formation inhibiting or its improving effect was observed. Further, Composition (5) containing lecithin showed higher scores and gave a result of better feeling on use than Composition (1) which is free of lecithin.

TABLE 7

| Test Composition | Score |
|---|---|
| Purified Water | 2.3 |
| Composition (1) | 3.7 |
| Composition (2) | 2.8 |
| Composition (3) | 4.4 |
| Composition (4) | 3.8 |
| Composition (5) | 3.6 |

Thus, the skin aging inhibitors and/or skin quality-improving agents and the cosmetic compositions of the present invention have the activity to promote epidermal cell proliferation, the activity to promote the fibroblast collagen synthesis, the activity to improve the moisture retention function of epidermis, activity to inhibit and/or to improve the wrinkle formation, and are proved to be effective for skin aging inhibition and/or skin quality improvement, and so on.

INDUSTRIAL APPLICABILITY

The skin aging inhibitors and/or skin quality-improving agents being effective for inhibiting skin aging and/or improving skin quality can be provided by the present invention. The skin aging-inhibiting, and/or skin quality-improving cosmetic compositions containing the skin aging inhibitors and/or skin quality-improving agents can be provided by the present invention. The method of inhibiting the skin aging and/or improving the skin quality which comprises applying the skin aging inhibitors and/or skin quality-improving agents containing hydroxyproline, N-acylated hydroxyproline derivatives or salts thereof as an effective ingredient to skin can be provided by the present invention. The method of inhibiting the skin aging and/or improving the skin quality which comprises applying the skin aging inhibiting and/or skin quality-improving cosmetic composition containing hydroxyproline, N-acylated hydroxyproline derivatives or salts thereof to skin can be provided by the present invention. The use of hydroxyproline, N-acylated hydroxyproline derivatives or salts thereof for producing the skin aging inhibitors and/or skin quality-improving agents can be provided by the present invention. The use of hydroxyproline, N-acylated hydroxyproline derivatives or salts thereof for producing the skin aging inhibiting and/or skin quality-improving cosmetic compositions can be provided by the present invention. The use of hydroxyproline, N-acylated hydroxyproline derivatives or salts thereof for inhibiting the skin aging and/or improving the skin quality can be provided by the present invention.

What is claimed is:

1. A method of promoting the proliferation of epidermal cells, which comprises the steps of:
   (i) selecting a compound from the group consisting of trans-4-hydroxy-L-proline, N-acetyl-trans-4-hydroxy-L-proline, and salts thereof; and
   (ii) applying an effective amount of the compound onto skin.

2. A method of promoting the collagen synthesis of fibroblast, which comprises the steps of:
   (i) selecting a compound from the group consisting of trans-4-hydroxy-L-proline, N-acetyl-trans-4-hydroxy-L-proline, and salts thereof; and
   (ii) applying an effective amount of the compound onto skin.

3. A method of improving the moisture retention function of epidermis, which comprises the steps of:
   (i) selecting a compound from the group consisting of N-acetyl-trans-4-hydroxy-L-proline and salts thereof; and
   (ii) applying an effective amount of the compound onto skin.

4. A method of inhibiting or improving wrinkle formation, which comprises the steps of:
   (i) selecting a compound from the group consisting of N-acetyl-trans-4-hydroxy-L-proline and salts thereof; and
   (ii) applying an effective amount of the compound onto skin.

* * * * *